United States Patent
Theeuwes et al.

(10) Patent No.: US 7,438,701 B2
(45) Date of Patent: Oct. 21, 2008

(54) LOCAL CONCENTRATION MANAGEMENT SYSTEM

(75) Inventors: Felix Theeuwes, Los Altos Hills, CA (US); Su Il Yum, Los Altos, CA (US)

(73) Assignee: Durect Corporation, Cupertino, CA (US)

(*) Notice: Subject to any disclaimer, the term of this patent is extended or adjusted under 35 U.S.C. 154(b) by 0 days.

(21) Appl. No.: 09/917,181

(22) Filed: Jul. 26, 2001

(65) Prior Publication Data

US 2003/0032942 A1   Feb. 13, 2003

(51) Int. Cl.
*A61M 29/00* (2006.01)
(52) U.S. Cl. .................. 604/96.01; 604/93.01
(58) Field of Classification Search .............. 604/93.01, 604/28, 30, 27, 502, 508, 509, 507, 264, 604/103.01, 103.02, 101.03, 96.01, 95.01, 604/101.02, 181, 523, 534, 535, 537, 288.01
See application file for complete search history.

(56) References Cited

U.S. PATENT DOCUMENTS

| | | | | |
|---|---|---|---|---|
| 4,437,856 | A * | 3/1984 | Valli ........................... | 604/29 |
| 5,087,244 | A * | 2/1992 | Wolinsky et al. ............ | 604/509 |
| 5,221,260 | A * | 6/1993 | Burns et al. .................. | 604/99 |
| 5,607,696 | A | 3/1997 | Rivera et al. | |
| 5,609,885 | A | 3/1997 | Rivera et al. | |
| 5,783,213 | A | 7/1998 | Rivera et al. | |
| 5,842,971 | A * | 12/1998 | Yoon ........................... | 600/101 |
| 6,113,915 | A * | 9/2000 | Aoki et al. ................ | 424/236.1 |
| 6,500,174 | B1 * | 12/2002 | Maguire et al. ............... | 606/41 |
| 6,551,290 | B1 * | 4/2003 | Elsberry et al. ............. | 604/284 |

OTHER PUBLICATIONS

Michaels et al. "A Thermodynamic Method of Predicting the Transport of Steroids in Polymer Matrices," AIChE Journal (1975) 21:1073-1080.

* cited by examiner

*Primary Examiner*—Ann Y Lam
(74) *Attorney, Agent, or Firm*—Thomas P. McCracken; David J. Abraham

(57) ABSTRACT

The invention provides a local concentration management system (LCMS) for delivery of highly concentrated therapeutic agent formulations. The LCMS comprises a device comprising an elongate body defining a lumen between its proximal and distal ends, and a diffuser element, a dilutor element, or both. The diffuser element, which is selectively permeable to the agent, is operatively associated with the elongate body so that agent flows through the elongate body, and into and through the diffuser element to exit the system. The dilutor element can be operatively associated with the system to be in fluid communication with the elongate body lumen, a diffusion space defined by a diffuser element inner wall, or both. The dilutor element is selectively water permeable, but substantially impermeable to agent, to provide for dilution of the agent during transit through the system. The LCMS system is designed to disperse and/or dilute the drug delivery stream.

18 Claims, 5 Drawing Sheets

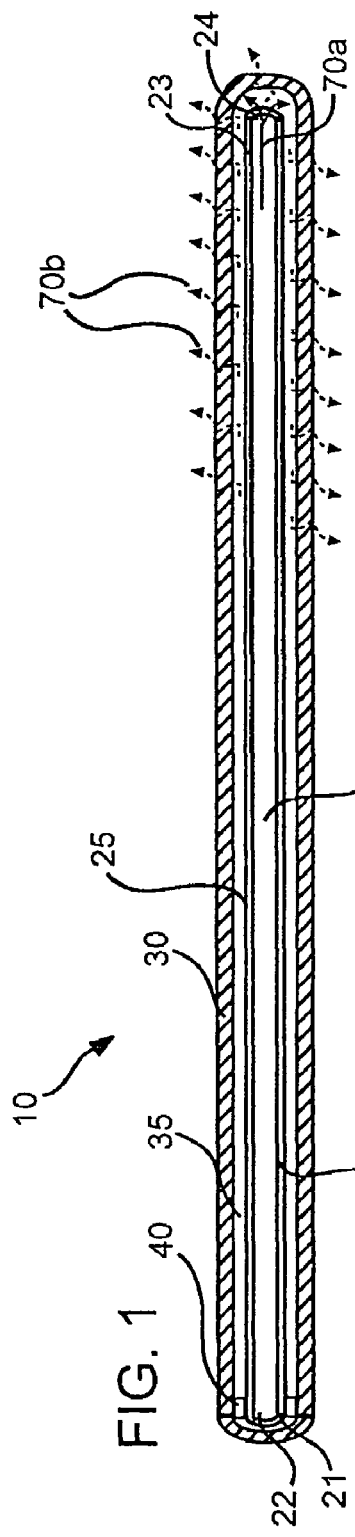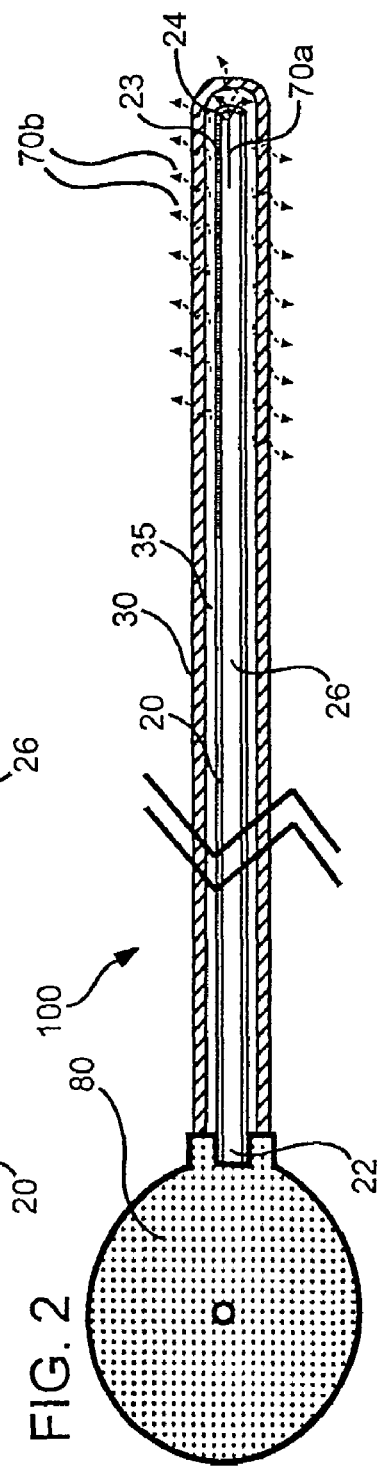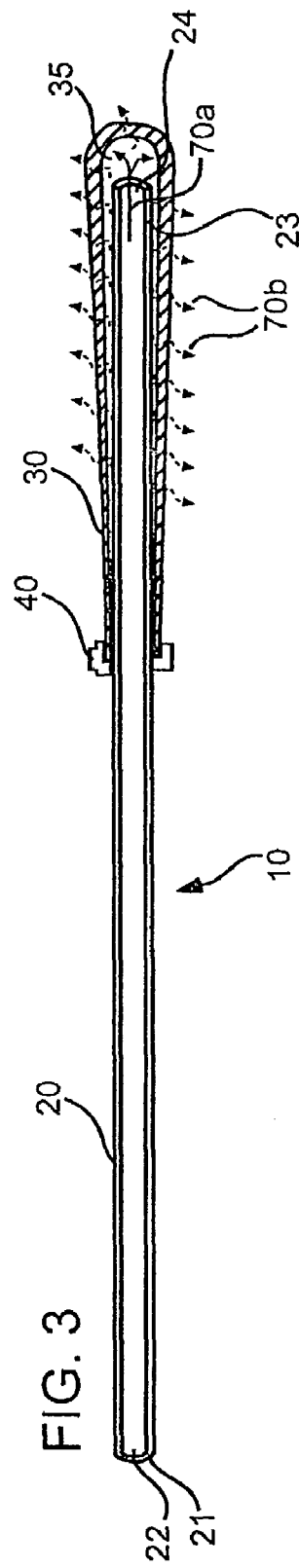

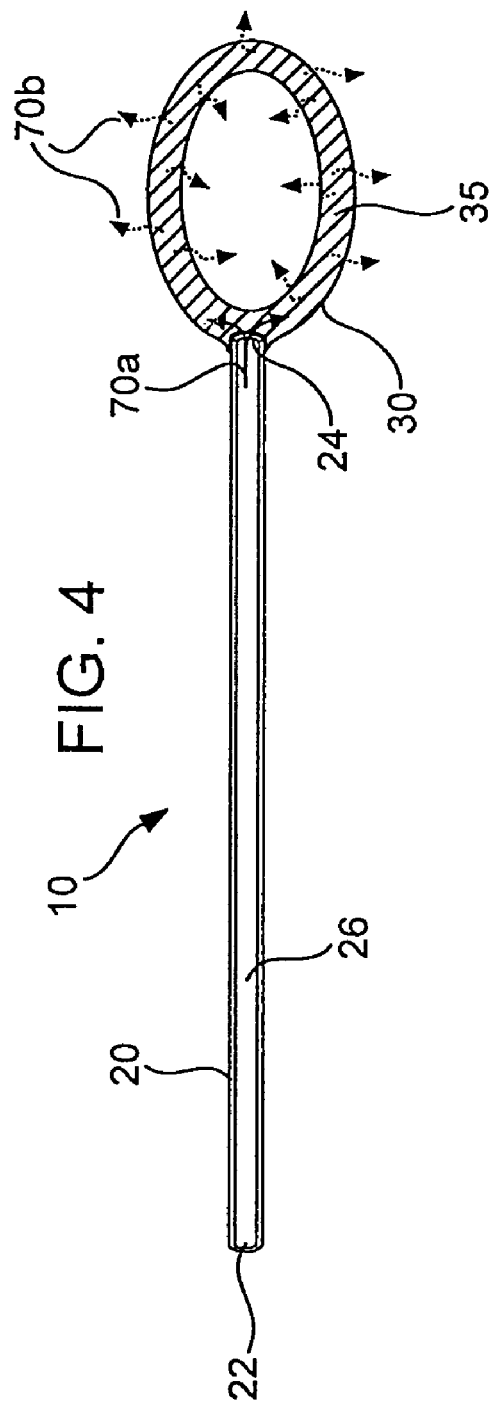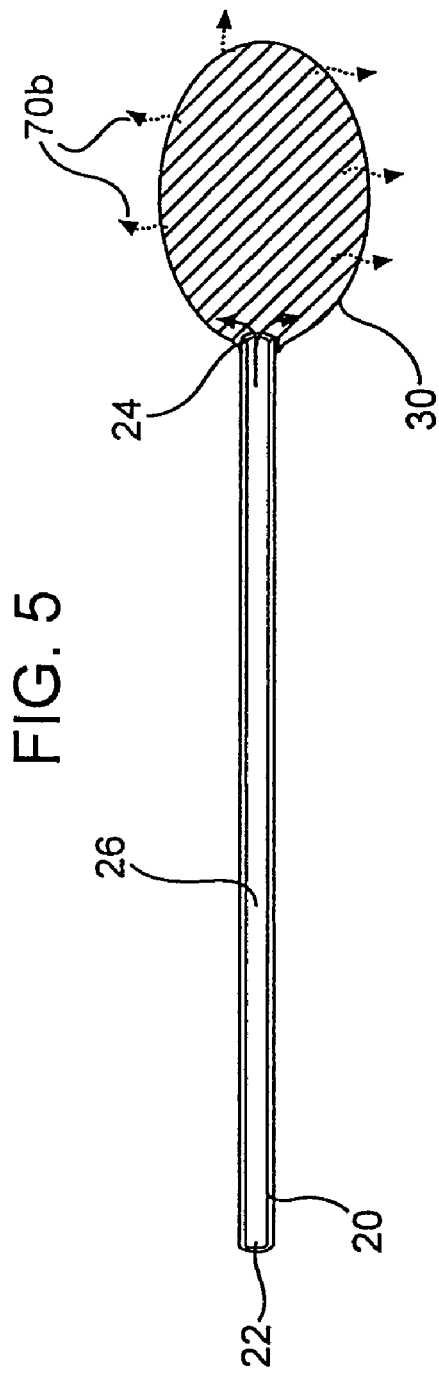

LOCAL CONCENTRATION MANAGEMENT SYSTEM

FIELD OF THE INVENTION

This invention relates generally to drug delivery devices and methods of use relating to same, and more particularly relates to a device suitable for delivery of highly concentrated agent formulations.

BACKGROUND OF THE INVENTION

Precise and accurate delivery of drugs or therapeutic agents to a specific treatment site within a subject represents a substantial challenge in the design of drug delivery systems. Site-specific drug delivery can be particularly challenging when the drug is to be delivered to the subject long-term, e.g., over several hours to several days, weeks or months.

One approach to long-term site-specific drug delivery involves the use of implantable delivery systems, e.g., biodegradable or osmotically-driven drug delivery devices (see e.g., U.S. Pat. Nos. 5,607,696, 5,609,885, and 5,783,213. While these implantable systems avoid the need for repeated injections often associated with long-term drug therapy administration, they have a number of limitations. First, the treatment sites which they can access are limited. Second, sites to which drug delivery is required can be fragile, sensitive or inaccessible and thus often not amenable to insertion of an implant. Third, the size of the delivery device can be impractical for long-term treatment regimes as the reservoir of the device that holds the drug either needs to be large enough to hold sufficient quantities of drug for the course of treatment or, alternatively, allow re-filling with drug during the course of the treatment. The latter is especially troubling as manipulating, re-filling and re-positioning these implantable devices can have serious consequences, e.g., increased risk of infection, patient discomfort, and increased costs.

Difficulty in delivery of drugs or agents to inaccessible locations of the body has been addressed in part by the use of catheters attached to drug delivery devices. For example, the distal end of such a catheter can be positioned at the desired site of delivery in the body, with the catheter acting as a conduit for the drug or desired agent from the drug delivery device. This configuration allows access to previously inaccessible sites, but these devices face many of the same issues as the traditional drug delivery devices, such as catheter size and toxicity at the delivery site.

An alternative approach is to provide formulations having high concentrations of drug, such that delivery of small amounts of formulation are sufficient to provide for a desired therapeutic effect. The total amount of formulation required for long-term therapy is thus substantially decreased, thus minimizing the size requirements for the reservoir of the device used to accomplish delivery. While this approach has met with some success, there are still serious limitations for certain therapeutics and for chronic delivery. For example, formulations with high concentrations of drug can be toxic to cells at the delivery site, or can result in irritation, inflammation, and tissue damage at the delivery site. Often formulating drugs at such high concentrations requires the use of very high or very low pH solutions, which alone can cause adverse side effects, particularly at the delivery site.

There is thus a need in the field for drug delivery devices which allow the use of a smaller drug reservoir and highly concentrated drug formulations, and that provide for safe delivery to a treatment site for long-term therapy.

SUMMARY OF THE INVENTION

The present invention provides a local concentration management system for delivering a highly concentrated therapeutic agent formulation. The system comprises a device comprising an elongate body defining a lumen between its proximal and distal end, and further comprising a diffuser element, a dilutor element, or both. The diffuser element, which is selectively permeable to the agent, is operatively associated with the elongate body so that agent flows through the elongate body, and into and through the diffuser element to exit the system. The dilutor element can be operatively associated with the system so as to be in fluid communication with the elongate body lumen, a diffusion space defined by a diffuser element inner wall, or both. The dilutor element is selectively water permeable, but substantially impermeable to agent, thus providing for dilution of the agent during transit through the system.

In various embodiment, the diffuser element can be associated with the elongate body in a variety of configurations, including attachment along the elongate body, attachment at the distal end of the elongate body (e.g., in the form of a "cup" or "hat"), and/or attachment to a separate structure that keeps the elongate body and diffuser element in a defined association (e.g., attachment to a drug delivery device). The elongate body can be provided within the body of a drug delivery device (e.g., the elongate body serves as the drug delivery device exit outlet or orifice) or is an extension of a drug delivery device orifice as a permanently or removably attached element.

In further embodiments, the dilutor element is associated with the elongate body, the diffuser element, or both in a variety of configurations. For example, the dilutor element can be provided as a portion of the elongate body wall so that an inner wall of the dilutor element is in fluid communication with the elongate body inner lumen, thus providing for ingress of water into the inner lumen and dilution of formulation as it passes through the elongate body. In another embodiment, the dilutor element is positioned within the diffuser element, to provide for ingress of water during the course of diffusion of formulation out of the device. In another embodiment, the dilutor element and the diffuser element are provided as a single element, such that the same element provides for both ingress of water from the environment of use and diffusion of agent out of the device.

In one aspect, the device is provided in connection with a drug delivery device to comprise a drug delivery system whereby the drug delivery device and the device are in fluid communication. Such a drug delivery system thus comprises; a drug delivery device; and a device comprising a catheter comprising an elongate body with an inner lumen and a diffuser element, with the elongate body and the diffuser element associated so that a formulation flows through the elongate body and out through the diffuser element. Alternatively, the device comprises a catheter operatively associated with a dilutor element positioned so as to provide for fluid communication between the elongate body inner lumen and an inner wall of the dilutor element such that formulation that flows through the elongate body inner lumen is diluted by water that enters the lumen via the dilutor element prior to exit from the device In another embodiment, the device comprises a catheter operatively associated with both a diffuser element and a dilutor element, which elements may be provided as separate elements or combined as a single element.

The drug delivery device may be completely or partially implantable, or may be retained at a site external to the body with at least a distal portion of the catheter implanted to direct the agent to the desired delivery site within the body. An exemplary drug delivery device for use in the system is configured to have at least one compartment for storing the formulation, e.g., a reservoir.

In another aspect, the present invention provides a method for delivery of a drug or therapeutic agent to a treatment site in a subject by implanting at least the distal end of a device of the invention at a desired delivery site and introducing an agent into the elongate body inner lumen to provide for delivery to a delivery site. By providing for diffusion of the agent over a greater surface area at the delivery site, and optionally dilution via the dilutor element during flow of formulation prior to delivery, the device helps to reduce side effects that may be caused by delivery of a concentrated agent to a site.

In other aspects, the invention provides a method for diluting the concentration of an agent exiting a device by implanting at least a distal portion of a local concentration management device at a delivery site in a subject, and introducing a formulation comprising an agent at a first concentration into the inlet of the elongate body. The introduced agent flows through the elongate body passageway, out the local concentration management device and to the delivery site in the subject, such that the agent in the formulation at the delivery site is diluted to a second concentration that is less than the first agent concentration. In related embodiments, the local concentration management device comprises a dilutor element, and the agent formulation is diluted during transit through the device. (e.g., the agent in the formulation is diluted from a first, higher concentration to a second, lower concentration prior to exit at the delivery site).

In another aspect, the invention features a method for dispersing a drug delivery stream by implanting at least a distal portion of a local concentration management device at a delivery site in a subject, and introducing a formulation comprising an agent at a first concentration into the inlet of the elongate body. The introduced agent flows through the elongate body passageway, out the local concentration management device and to the delivery site in the subject in a pattern that is disperse relative to a delivery pathway through the device. The dispersed agent formulation is thus diluted to second, lower concentration within fluids at the delivery site.

A primary object of the invention is to provide a device that can control the local concentration of agent at a desired delivery site.

Another object of the invention is to provide a device that can be used to deliver formulations comprising high concentrations of a drug or other agent with minimal detriment to the surrounding tissue.

It is another object of the invention to provide a mechanism by which the delivery of drug will be over a greater surface area compared to conventional devices.

Another object of the invention is to provide a drug delivery system that can be readily handled, implanted and adapted for use in accurate, consistent and reliable delivery of drug at a particularly low volume rate, e.g., microliter or submicroliter quantities of a formulation per day.

It is yet another object of the invention to provide a drug delivery system compatible for use with a highly concentrated drug formulation so that a smaller volume of drug is required to provide a therapeutic effect, thereby reducing the volume of formulation that must be stored in the drug delivery device. This permits reduction in size of the entire drug delivery device, thus increasing comfort and mobility for the patient.

It is another object of the invention to provide a device that is suitable for delivery of drug to a distal delivery site within a subject, particularly sites that are highly sensitive or fragile, e.g., the spinal cord.

Another object of the invention is to provide a device that can be used with a variety of drug delivery devices.

An advantage of the invention is that the local concentration management system can facilitate delivery of extremely small volumes of drug, e.g., submicroliter volumes, and at low volume delivery rates, yet is easily handled, e.g. by a clinician during implantation.

Another advantage of the invention is that the device can release concentrated drugs, drug formulations or other agents in a diffusive manner and/or over an extended surface area, thereby reducing the local concentration of the agent released. In this regard the invention helps to avoid potentially harmful side effects caused by interaction of the compound released with the surrounding tissues and bodily fluids. This advantage; thus decreasing toxicity, irritation and other side effects to the surrounding tissue exposed to the drug or agent.

A further advantage of the invention is that the device helps prevent precipitation of the drug or agent in the outflow area of the drug delivery device. This provides for more consistent drug delivery, reduced stress placed on the drug delivery device, and increased life expectancy of the drug delivery system, with a concomitant decrease in the frequency of required repairs to the drug delivery system and drug replenishment.

Another important advantage of the invention is that concentrated drug, drug formulation or other agent stored in the drug delivery device can be diluted prior to delivery to a delivery site allowing concentrated formulations to be stored while allowing the formulations to be delivered in a manner which decreases irritation and other side effects to the surrounding tissue exposed to the drug or agent.

It is another advantage of the invention that the delivery system prevents back diffusion of the released drug or agent and prevents entry of fluids or compounds from outside the device to the inside.

These and other objects, advantages and features of the present invention will become apparent to those skilled in the art upon reading this disclosure in combination with the drawings, where like numerals refer to like components throughout.

BRIEF DESCRIPTION OF THE DRAWINGS

FIGS. 1 and 3 are cut-away views of a local concentration management system of the invention comprising an elongate body operatively attached to a diffuser element.

FIG. 2 is a partial cut-away view of a drug delivery system comprising a drug delivery device and a local concentration management system of the invention.

FIG. 4 is a cut-away view of a local concentration management system of the invention comprising an elongate body operatively attached to a ring-like diffuser element.

FIG. 5 is a cut-away view of a local concentration management system of the invention comprising an elongate body operatively attached to a bulb-like diffuser element.

DETAILED DESCRIPTION OF THE INVENTION

Figure 6:
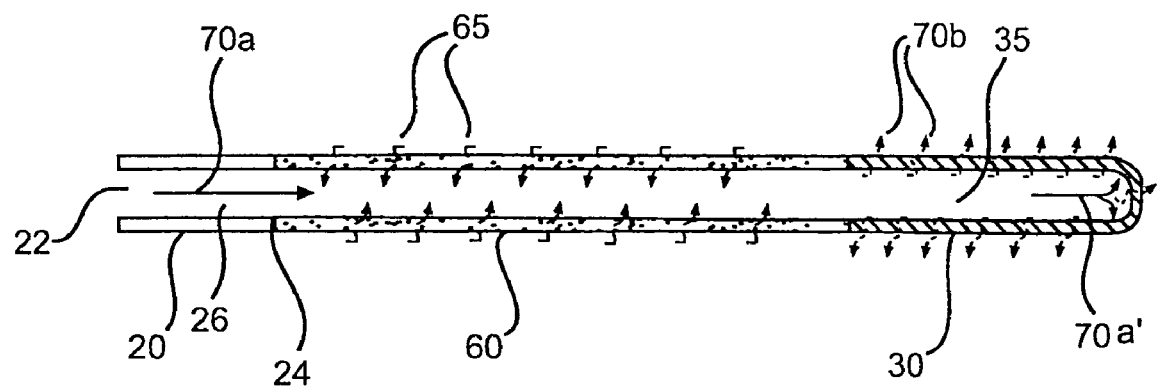
FIG. 6 is a cut away view of a local concentration management system of the invention comprising a dilutor element and a diffuser element.

Before the present invention is described, it is to be understood that this invention is not limited to the particular embodiments described, as such may, of course, vary. It is also to be understood that the terminology used herein is for the purpose of describing particular embodiments only, and is not intended to limit the scope of the present invention, which will be limited only to the appended claims.

It must be noted that as used herein and in the appended claims, the singular forms "a", "an," and "the" include plural referents unless the context clearly dictates otherwise. Thus, for example, reference to "a catheter" includes one or more catheters within an assembly, reference to "a formulation" includes mixtures of different formulations, and reference to "the method of delivery" includes reference to equivalent steps and methods known to those skilled in the art, and so forth.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated by reference to disclose and describe the specific methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "delivery site" is generally meant to refer to the specific area of the body to which the drug, drug formulation, or other agent is introduced, i.e. through a device of the present invention. The delivery site may be a discrete area (e.g., an area at the distal tip of the device) or a somewhat larger area surrounding the device (e.g., the device provides for delivery along either a portion of or the entire length of the assembly).

The terms "treatment site" or "target site" as used herein interchangeably to mean the desired site of action of the substance to be delivered. The treatment site may be the substantially the same as the delivery site, or may be some distance from it (e.g., adjacent to the delivery site, or within a distance from the delivery site that can be reached by diffusion or other transport of drug from the delivery site).

The terms "access site" or "implantation site" as used herein are generally meant to refer to a site on or in a subject at which a drug delivery system of the invention is introduced for implantation and positioning within the subject's body, e.g., for delivery of drug to a desired delivery site. For example, where a device is for delivery of drug to the spinal cord, the access site or implantation site can be a subcutaneous site at which a proximal end of the device is substantially retained (i.e., with the drug delivery device), and the delivery site is in a position within or adjacent the spinal cord at which a distal end of the device is positioned for delivery of drug.

The term "drug delivery device" as used herein is generally meant to encompass any device that comprises a drug reservoir and that facilitates movement of drug from the drug reservoir to a site external to the drug delivery device. "Drug delivery device" thus encompasses controlled drug delivery devices, as well as devices that release drug in an unpatterned, e.g., substantially unregulated, manner. Controlled drug release devices are particularly preferred for use with the device of the present invention.

The term "local concentration management system" of "LCMS" as used herein refers to a device of the invention minimally comprising 1) an elongate body defining a lumen extending between and communicating proximal and distal ends of the elongate body; and 2) a diffuser element, a dilutor element, or both. The LCMS of the invention can be combined with a drug delivery device to provide for delivery of drug in a manner that provides for delivery of an agent formulation in a manner that controls the local concentration at the delivery site.

The term "delivery system" as used herein is generally meant to refer to a combination of a device of the invention (e.g., an elongate body, a diffuser element, a dilutor element, or both) and a drug delivery device suitable for use in the delivery of drug to a delivery site, preferably a controlled release device.

The term "diffusion barrier" as used herein is generally meant to refer to the physical region(s) of the diffuser element which is responsible for egress of the formulation to the delivery site, e.g., a shell or membrane which is in direct contact with the environment outside the diffuser element. The diffusion barrier may be composed of a material that allows diffusion of the formulation, while controlling the levels of biological fluids that enter into the diffuser element. The diffusion barrier may also be of a composition that allows an alteration of the activity of the drug as it passes through the diffusion barrier.

The term "diffuser element" as used herein refers to the structure of the local concentration management system that is responsible for controlling the egress of a drug, drug formulation or agent to a delivery site and/or the concentration or activity of the formulation following exit from the elongate body prior to introduction to the delivery site. The diffuser element comprises at least a diffusion barrier and a diffusion space (i.e., that area between the diffusion barrier and the elongate body), through which drug is diffused. The diffuser element may also include a second formulation that alters the activity or dilution of the therapeutic formulation following exit of the formulation from the elongate body, thus altering either the concentration of the therapeutic formulation or the activity of the therapeutic agent within the diffuser element prior to introduction to the delivery site.

The term "dilutor element" as used herein refers to an element that provides for ingress of water into a formulation flow pathway to dilute an agent formulation during its transit through the flow pathway.

The term "impermeable" as used herein is generally meant to refer to material that is sufficiently impermeable to environmental fluids as well as ingredients contained within the dispensing device such that the migration of such materials into or out of the device through the impermeable portion of the device is so low as to have substantially no effect on the concentration, activity or function of the drug retained within the device during the delivery period.

The term "selectively permeable" as used herein is meant to refer to material that is substantially impermeable to one or more compounds, but substantially permeable to a different compound(s). For example, a material is selectively permeable for a drug when the materials allows for passage of the drug, but does not allow substantial or detectable passage of environmental fluids or agents in the fluid. In another example, a material is selectively permeable to water when the material allows passage of water, but does not allow substantial or detectable passage of other compounds (e.g., drug).

The term "controlled release" as used herein (e.g., in the context of "controlled drug release") is generally meant to encompass release of substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

The term "controlled release device" as used herein is generally meant to encompass any device that provides for release of a drug or other desired substance in a manner that is at least substantially independent of its environment of use, and that can be adapted for use with a device of the invention.

The term "low volume rate delivery" as used herein is generally meant to refer to delivery of a liquid or semisolid drug at a volume rate of from about 0.01 µl per day to about 200 µl per day, usually about 0.04 µl per day to about 20 µl per day, more usually about 0.1 µl per day or about 1.0 µl per day.

The terms "distal" or "distal end" as used herein is generally meant to refer to components and/or structures which are closer to the delivery site, treatment site or sampling site within the body of the subject being treated.

The term "proximal" or "proximal end" as used herein is generally meant to refer to components and/or structures which are closer to a clinician or individual who is using the device of the invention in a medical treatment setting.

The term "drug formulation", "agent formulation," or "formulation" as used interchangeably herein are generally meant to encompass any substance suitable for delivery to a treatment site of a subject, which substances can include pharmaceutically active drugs, as well as biocompatible substances that do not exhibit a pharmacological activity in and of themselves, but that provide for a desired effect at a treatment site, e.g., to flush or irrigate a treatment site, e.g., saline. Such drugs and/or biocompatible substances may be in an active or inactive state.

The terms "drug" or "agent" as used interchangeably herein are generally meant to refer to any drug that is conventionally administered by injection (e.g., intravenously, intramuscularly, subcutaneously, intrathecally, etc.). Drugs compatible for delivery using the devices and methods of the invention are readily apparent to the ordinarily skilled artisan upon reading the disclosure provided herein.

The term "drug delivery" as used herein is generally meant to refer to a process by which drugs or other therapeutic agents are released from devices of the invention. "Drug delivery" is thus meant to include, applying agents to areas including, although is not necessarily limited to, a subcutaneous, percutaneous, intravenous, intrathecal, intramuscular, intra-arterial, intravascular, intraperitoneal, intraspinal, epidural, intracranial, peritumoral, or intratumoral (e.g., within a cancerous growth) tissues within a subject, as well as to areas within or near a selected organ or tissue (e.g., central nervous system (e.g., spinal fluid, brain, etc.), peripheral nervous system, kidney, liver, pancreas, heart (e.g., intrapericardial), lung, eye, ear (e.g., inner ear), lymph nodes, breast, prostate, ovaries, testicles, thyroid, spleen, etc.), digestive system (e.g., stomach, gastrointestinal tract, etc.), skeletal muscle, bone, urinary bladder, gall bladder, adrenal gland, adipose tissue, parathyroid gland, uterus, fallopian tube, skin, into a vessel associated with the circulatory system (e.g., artery, arteriole, blood vessel, vein, capillary bed, lymph vessel, particularly arteries that feed a selected organ or tissue)), a tumorous growth (e.g., cancerous tumor (e.g., solid tumor), cyst, etc.), or at an area associated with a microbial infection (e.g., bacterial, viral, parasitic or fungal infection), or to an autologous or synthetic graft (e.g., a vascular graft).

The term "site-specific drug delivery" as used herein is generally meant to refer to any process by which drugs or other therapeutic agents are released from a device to a target area in need of medication. Site-specific drug delivery meant to include, but is not necessarily limited to, therapeutically applying agents to areas comprising subcutaneous, percutaneous, intravenous, intrathecal, intramuscular, intra-arterial, intravascular, intraperitoneal, intraspinal, epidural, intracranial, peritumoral, or intratumoral (i.e., within a cancerous growth) tissues within a subject, as well as areas within or near a selected organ (e.g., central nervous system (e.g., spinal fluid, brain, etc.), peripheral nervous system, kidney, liver, pancreas, heart (e.g., intrapericardial), lung, eye, ear (e.g., inner ear), lymph nodes, breast, prostate, ovaries, testicles, thyroid, spleen, etc.), digestive system (e.g., stomach, gastrointestinal tract, etc.), skeletal muscle, bone, urinary bladder, gall bladder, adrenal gland, adipose tissue, parathyroid gland, uterus, fallopian tube, skin, into a vessel associated with the circulatory system (e.g., artery, arteriole, blood vessel, vein, capillary bed, lymph vessel, particularly arteries that feed a selected organ or tissue)), a tumorous growth (e.g., cancerous tumor (e.g., solid tumor), cyst, etc.), or at a site associated with a microbial infection (e.g., bacterial, viral, parasitic or fungal infection), or to an autologous or synthetic graft (e.g., a vascular graft).

The term "subject" as used herein is generally meant to refer to any animal to which a drug, drug formulation or an agent can be delivered, including but not necessarily limited to, a mammal (e.g., human, dog, cat, cow, etc). In one embodiment of interest, the subject is human.

The term "unintended result" as used herein is generally meant to refer to any undesirable or unanticipated reaction that would have an adverse impact on the activity or function of the drug to be delivered.

Overview of the Invention

The present invention provides a device useful in the administration of a formulation having a high concentration of agent or other component in the formulation. The device generally comprises an elongate body with an inner lumen extending between a proximal and a distal end. The distal end of the elongate body defines at least one delivery outlet. In general, the device is a catheter operatively associated with a diffuser element, a dilutor element, or both a diffuser element and a dilutor element.

The device of the invention is particularly adapted to facilitate the delivery of drug(s) or drug formulations to sites distal to the drug source, e.g., from an implanted drug delivery device. For example, the device may be navigated through a biologically defined lumen of the subject, e.g., the vasculature or the like, and positioned at a desired delivery site within the vascular system. A drug delivery device compatible and in fluid communication with the device is positioned either internal or external to the subject, often times implanted within the subject, and the formulation is delivered via a pathway through which drug may flow from the drug reservoir of the drug delivery device to the device assembly. In certain embodiments, concentrated drug is contained within the drug reservoir, whereby the concentrated drug passes from the drug delivery device, into the inner lumen of the device assembly, out the lumen of the elongate body to the diffuser element, and from the diffuser element to the delivery site. Preferably, the concentrated drug is diluted before delivery and/or delivered over an increased surface area. In a specific embodiment, the drug is contained in the drug reservoir in an inactive state and is converted to an active state prior to delivery.

The device of the invention and its components are described below in more detail.

Dilutor Element

In one embodiment, the device of the invention has both a diffusion element and a dilutor element. The dilutor element generally comprises a material that is selectively water permeable, but substantially impermeable to formulation components, particularly to agent in the formulation, more particularly to ionized drug molecules or formulation agents. The dilutor element thus serves to provide for dilution of formulation during its transit through the device.

The dilutor element can provided as a portion of a wall of the elongate body or all or a portion of the diffuser element. In one embodiment, a single element provides the functions and characteristics of both the dilutor and diffuser elements (e.g., the dilutor and diffuser elements are combined into a dilutor/diffuser element that provides for both ingress of water to dilute the formulation, and egress of formulation out of the element by diffusion). The dilutor element is generally positioned so as to be in fluid communication with the lumen of the elongate body, with the diffusion space defined by the diffuser element inner wall, or both. In use, water from the environment in which the device is implanted passes through the selectively water permeable material of the dilutor element, resulting in dilution of the formulation components during transit of the formulation through the device. At the same time, the volume of diluted formulation increases in proportion to the osmotic water influx and length of the selectively water permeable portion of the modifying element wall. The increase in volume can be adjusted or accommodated by, for example, the diffusion space defined by the diffuser element.

Suitable dilutor elements for use in the invention are further described in the U.S. patent application entitled "Catheter For Modification Of Agent Formulation,", filed on the same date as the instant specification) and incorporated herein by reference in its entiretey, in which modifying elements that provide for dilution of the formulation during its transit through a catheter are described.

Elongate Body

The elongate body generally comprises a proximal end, a distal end, and a passageway defining an inner lumen between the proximal and distal ends. Generally, the shape of the elongate body is substantially tubular. The shape may vary depending on a variety of factors such as patient anatomy, delivery site, delivered drug, and the like. Shapes that may find use in the present invention include, but are not limited to, elliptical, cylindrical, or the like.

The elongate body can be provided within the body of a drug delivery device, e.g., the elongate body is all or at least a part of a drug delivery device exit outlet or orifice defined by a drug delivery device. Alternatively, the elongate body can be provided as an extension of a drug delivery device orifice as a permanently or removably attached element, e.g., in a "catheter" configuration.

Where the elongate body is not provided within a drug delivery device (e.g., the elongate body is provided as a removable or fixedly attached catheter-like element for use with a drug delivery device), the elongate body is generally made of a highly compliant, material. Where a portion of the elongate body is exposed to tissue upon implantation (e.g., a portion of the elongate body in a catheter configuration is not covered by a diffuser element), then the elongate body material comprises a biocompatible material for at least that portion which is implanted. The compliant characteristic of the elongate body enables safe navigation to a delivery site, e.g., through tortuous biologically defined lumens or preformed conduits and the like, and to minimize damage to surrounding tissue or structures. As such, the elongate body can be of substantially the same degree of flexibility or stiffness throughout its length, or may vary in flexibility or stiffness over its length. The desired flexibility or stiffness of the elongate body can be varied with the particular delivery site and/or drug delivery pathway with which it is to be used.

The elongate body can comprise one or more than one piece, component, material or layer. Such multiple pieces, components, materials or layers may be contiguous, partially overlapping, discretely layered, extruded, or the like and may be subsequently attached using any suitable means. The elongate body can comprise discrete sections of differing materials and/or layers to impart various desirable characteristics. Exemplary materials include, but are not necessarily limited to: biocompatible polymers, elastomers, metals, metal alloys, glasses, laminates of hydrophilic polymers and hydrophobic polymers, multilaminates or polymers, metal, and/or glasses, and the like.

In general, any portion of the elongate body that is exposed to the environment of use is substantially impermeable to formulation components Where the elongate body is substantially impermeable, the elongate body is operably associated with a diffuser element, as described in more detailed below. At least a portion of the elongate body generally comprises a polymer that renders the elongate body substantially impermeable to water. In general, a polymer is substantially impermeable to water when the water sorption of the polymer is less than 5%.

Exemplary biocompatible polymeric materials useful for a substantially impermeable elongate body include, but are not necessarily limited to, homopolymers and copolymers of vinyl acetate (e.g., ethylene vinyl acetate copolymer); homopolymers and copolymers of acrylates (e.g., poly(methyl) methacrylate (PMMA), polyethylmethacrylate, ethylene glycol dimethacrylate, ethylene dimethacrylate and hydroxymethyl methacrylate); polyurethanes; polyethylenes; polyvinylchlorides; polycarbonates; polyamides; polysulfones; polyesters; polyimides; halogenated polymers (e.g., polytetrafluoroethylene (PTFE), polyvinyl fluoride, polychlorotrifluoroethylene, copolymers tetrafluoroethylene and hexafluoropropylene; PFA, and the like); polyolefins (e.g., high density polyethylene (HDPE), low density polyethylene (LDPE), linear low density polyethylene (LLDPE), polypropylenes, and the like); polystyrenes; nylons; homopolymers and copolymers of acrylonitrile (e.g., acrylonitrile-butadiene-styrene polymer, styrene acrylonitrile, polycarbonate-acrylonitrile-butadiene-styrene; and the like);

polyvinylpyrrolidone; polyacrylonitrile butadiene; polyethylene terephtholate; polymethylpentene; polyisobutylene; polymethylstyrene; polyvinylidine chloride and homopolymers and copolymers of polyvinylidine chloride (e.g., polyvinylchloride-acrylic copolymers); PEBAX; HYTREL; and other similar compounds known to those skilled in the art. Further exemplary polymers are described in Plastics Materials 6th ed., May 1995, J. A. Brydson, Butterworth-Heinemann, publishers.

Suitable, biocompatible elastomers include, but are not necessarily limited to, biocompatible elastomers such as medical grade synthetic (e.g., silicone) rubbers; polyvinyl chloride elastomers; polyolefins; homopolymeric and copolymeric elastomers; natural rubbers; and fluorinated polymers (e.g., PTFE), and the like.

Metallic materials suitable for the elongate body comprise stainless steel, titanium, platinum, tantalum, gold and their alloys; gold-plated ferrous alloys; platinum-plated titanium, stainless steel, tantalum, gold and their alloys as well as other ferrous alloys; cobalt-chromium alloys; titanium nitride-coated stainless steel, titanium, platinum, tantalum, gold, and their alloys; nickel titanium; and superelastic nickel titanium.

In one particular embodiment, the elongate body comprises nickel titanium materials, particularly superelastic nickel titanium (NITINOL™).

In general, the material from which the elongate body is made is substantially impermeable and/or completely impermeable to formulation and formulation components (e.g., agent) to be delivered through the elongate body passageway. The elongate body materials are generally selected so that they do not unintentionally react with the drug or agent to be delivered.

The elongate body may comprise additional materials, components additives or agents as well. For example, the inner lumen wall may comprise a coating to facilitate transport of drug through the lumen, or to impart other desirable characteristics. The lumen can also comprise coatings that reduce the risk of infection, e.g., a silver coating, an antimicrobial agent(s), or the like. Similarly, the outer wall of the elongate body can comprise a coating or be treated to facilitate lubriciosness, reduce the risk of infection and/or to impart other desirable characteristics to the device. Markers or other such material may also be added to facilitate radiographic visualization of the elongate body. For example, materials such as platinum, palladium, gold or radiopaque filler materials such as barium sulfate, bismuth trioxide, bismuth carbonate, powdered tantalum, or the like may be incorporated. Similarly, the elongate body may comprise a reinforcement element(s) to provide for enhanced stiffness, to avoid kinking of the elongate body, etc. Such reinforcement element(s) can be, for example, a coil or braid that is on the outer surface of the elongate body, within a wall of the elongate body, or positioned on the inner wall of the elongate body.

As noted above, the elongate body defines an inner lumen or passageway, through which drug or agent is delivered. Such lumen generally lies between the proximal and distal ends and of the elongate body. In certain embodiments, the elongate body defines a single lumen; however, the elongate body may also define multiple lumen, which may vary in length and/or diameter. Where more than one lumen is present, the lumens may be contiguous, adjacent, or branching. The lumen(s) transports drug to an aperture of the elongate body for expulsion out of the elongate body.

Similarly, the elongate body can define a single delivery outlet or aperture, or two or more such outlets or apertures. Where the elongate body defines a plurality of apertures, the apertures can be situated on various sites on the elongate body, and can vary in size. In one embodiment, the elongate body has a distal aperture and a plurality of side-apertures defined by the elongate body wall. Apertures may be complete, unobstructed holes, or may be partial holes. The elongate body distal end can comprise any of a variety of shapes, and may comprise a valve, e.g., a duck bill valve, or other element to further facilitate regulation of delivery of formulation through the elongate body outlet and to inhibit back-flow into the elongate body lumen. For example, a rate-limiting membrane or valve-structure can be positioned within an outlet to prevent back-flow and/or to facilitate a regulation of formulation flow out the outlet.

The dimensions of the elongate body, e.g., length, inner diameter, outer diameter, may vary and are generally selected as a function of various factors, e.g., the delivery site, the formulation to be delivered, and the like. The outer diameter may be substantially the same throughout the entire length or may vary, e.g., taper, step, or the like. The elongate body inner diameter may vary depending on a variety of factors, one such factor being drug compatibility, e.g., molecular weight, viscosity, and other factors such as drug delivery rates, and the like. For example, in certain embodiments, the inner diameter is compatible for drug delivery at relatively low volume rates, e.g., as low as about 0.01 µl per day. Conversely, the inner diameter may be compatible for relatively higher volume rates. In certain embodiments, the rate of drug delivery ranges from about 0.01 µl per day to 300 µl per day, usually between about 0.02 µl per day to 250 µl per day. The inner diameter of the elongate body can be substantially the same throughout the entire length, or it may vary, e.g., it may be tapered, stepped or narrowed at any point along the length. For example, the inner diameter may be tapered at the distal end or widened at any point along the length, e.g., widened over a distal portion. In an exemplary, non-limiting embodiment, the length of elongate body ranges from about 0.1 inches to 80.0 inches, usually from about 2.0 inches to 60.0 inches and more usually from about 6.0 inches to 24-30 inches. In certain embodiments, the elongate body inner diameter ranges from about 0.0002 inches to 0.02 inches, e.g., from about 0.0005 inches to 0.015 inches, usually from about 0.001 inches to 0.0125 inches and more usually from about 0.002 inches to 0.010 inches. Where the elongate body is provided as an exit orifice of a drug delivery device, the length of the elongate body is measured starting from the proximal end of the elongate body which is in fluid communication with the reservoir of the drug delivery device.

The elongate body outer diameter and consequentially the circumference of the elongate body, may vary as well. In certain embodiments, the elongate body outer diameter ranges from about 0.080 inches to about 0.020 inches, usually from about 0.020 inches to about 0.070 inches and more usually from about 0.01 inches to 0.100 inches, e.g., from about 0.015 inches to about 0.030 inches to 0.060 inches. In many embodiments, the outer diameter varies from the proximal end to the distal end, e.g., tapers in diameter or decreases or increases in a step-wise fashion. In particular embodiments, the inner diameter ranges from about 0.003 inches to 0.006 inches and the outer diameter ranges from about 0.005 inches to 0.012 inches Diffuser Element A diffuser element is operatively associated with the elongate body so as to define a diffusion space, which is in fluid communication with a passageway of the elongate body and an inner wall of the diffuser element. In use, formulation flows through the elongate body lumen, out the delivery outlet(s), into the diffusion space, and out the diffuser element. The diffuser element thus provides a greater surface area over which formulation exits the device, effectively "diluting" the formulation in the environment in which the devices is used.

The diffuser element facilitates dilution of formulation components by increasing the surface area over which the formulation is delivered. By "operatively associated" is meant a structural relationship between the elongate body and the diffuser element such that the components provide for flow of formulation through the elongate body passageway, into or through the diffuser element, and out the device.

The diffuser element can be associated with the elongate body in a number of ways, including attachment along all or a portion of the elongate body, attachment at the end of the elongate body, and/or attachment to a separate structure that keeps the elongate body and diffuser element in a defined association. The diffuser element provides diffuse delivery of formulation and/or agent over an extended surface area, thus effectively diluting the formulation or agent in the bodily fluids that surround the implanted device.

In an exemplary embodiment, the diffuser element is associated with the elongate body such that drug or therapeutic agent passes through the lumen of the elongate body and subsequently passes through the diffuser element to a delivery site. By "associated" is generally meant a structural relationship between the elongate body and the diffuser element such that they form a unit. For example, the diffuser element may be fixedly (e.g., permanently) attached or removably attached, connected, or the like, to some or all of the elongate body. Alternatively, both the elongate body and the diffuser element may be fixedly or removably attached to a third structural element (e.g., a drug delivery unit) such that the dimensional relationship of the diffuser element with the elongate body is maintained. Such fixed or removable attachment or connection may be accomplished by means of adhesion, pressure, molding, snap fit, male-female connection, threading, bonding, chemical, mechanical, or other such means.

The diffuser element is interrelated to the elongate body of the catheter in that the diffuser element surrounds the aperture(s) of the elongate body such that all of the formulation being introduced to the delivery site passes through the diffuser element upon exit from the elongate body. For example, a diffuser element may be attached or connected to the outer wall of the elongate body, such that the diffuser element forms an outer sheath or casing surrounding the aperture(s) of the elongate body. By sheath is meant enwraps a portion of the elongate body or substantially enwraps all of the elongate body. In another example, the diffuser element is attached to the very distal edge of the elongate body, such that the diffuser element forms a protrusion extending from the elongate body or covers the distal aperture(s) of the elongate body. In yet another example, both the elongate body and the diffuser element are attached to a third structure (e.g., a drug delivery device such as an osmotic pump), and the diffuser element surrounds the entire length of the elongate body. The device may be associated with a drug delivery device, to comprise a drug delivery system.

The diffuser element can sheathe substantially the entire or the entire length of the elongate body or a portion of the elongate body, e.g., the distal end. Where the diffuser element sheathes all or a portion of the elongate body, the diffuser element may be adapted to slideably receive the elongate body. Alternatively, the diffuser element can be provided as an extension of the distal end of the elongate body or a combination of the aforementioned. In one embodiment, the diffuser element is provided as one or more a bulb-like structure or a ring-like at the elongate body distal end.

The diffuser element may be fixedly or removably attached, connected, or the like, to some or all of the peripheral wall of the elongate body. Alternatively, both the elongate body and the diffuser element may be fixedly or removably attached to a third element (e.g., a drug delivery unit or an element adapted for attachment to a drug delivery device) such that the functional relationship of the diffuser element with the elongate body is maintained. Such fixed or removable attachment or connection may be accomplished by means of adhesion, pressure, molding, snap fit, male-female connection, threading, bonding, chemical, mechanical, or other such means.

Generally, the diffuser element is permeable or semi-permeable to the agent, and may also be permeable or impermeable to biological fluids from the external environment, such that the diffuser element permits egress of agent from the device assembly and to the delivery site, while inhibiting or substantially inhibiting ingress of agents contained in the biological fluids into the diffuser element.

As noted above, the diffuser element is generally adapted to allow for diffusion of formulation out of the device, to effectively dilute a formulation component (e.g., drug) in fluids at the delivery site, e.g., to avoid an unacceptably high local concentration of formulation component (e.g., agent) at the delivery site. The diffuser element can accomplish this in various ways. For example, the diffuser element can comprise a semipermeable membrane, which membrane provides for more dilute delivery of the agent over the delivery site, effectively resulting in dilution of the agent within the environmental fluids surrounding the diffuser element. Alternatively, the diffuser element may comprise multiple apertures through which the formulation passes, again providing for more diffuse delivery of the formulation at the delivery site and distribution/dispersion in the environmental fluids.

Diffuser element body materials can vary according to a variety of factors such as the desired permeability (e.g., selectively permeable to agent), stiffness, and the like. For the example, the diffuser element can be microporous, a dense membrane, or an ion-exchange membrane. Generally, the materials must be compliant and biocompatible.

The permeability of a formulation component (e.g., drug) through polymeric walls or membranes can be estimated from the relationship $DC_s$ and MP, where D is the diffusivity of an agent in the polymer and $C_s$ is the solubility in the polymer of the substance or agent in the formulation to be delivered, and MP is the melting point of the polymer. For a detailed discussion of this relationship and guidance as to the prediction of the transport of a substance through a polymeric material, see, e.g., Michaels et al "A Thermodynamic Method of Predicting the Transport of Steroids in Polymer Matrices," AIChE Journal (1975) 21:1073-1080.

Exemplary materials include: metal, metal alloy, carbon fiber, polycarbonate, polymer, plexiglass, stainless steel, parylene-coated stainless steel, Teflon-coated stainless steel, and nickel titanium; silicone elastomers of varying cross-link densities, polyurethane of varying ratios of hydrophilic/hydrophobic segments, thermoplastic polyester elastomer (Hytrel, Dupont), Ethylene vinyl acetate copolymers with vinyl acetate contents greater than or equal to 15 percent, and the like. Further exemplary materials include, but are not necessarily limited to, those biocompatible polymers described above for the elongate body. The diffuser element can comprise a microporous membrane, such as those described in, for example, U.S. Pat. Nos. 4,160,452 and 4,200,098.

The diffuser element may comprise additional materials, components additives or agents as well. For example, the inner or outer walls, i.e., the inner and outer walls of the diffusion element may comprise a coating to impart desirable characteristics e.g., coatings that reduce the risk of infection, e.g., a silver coating, an antimicrobial agent(s), or the like, or a coating to facilitate lubriciousness. Markers or other such material may also be added to facilitate radiographic visualization of the diffuser element. For example, materials such as platinum, palladium, gold or radiopaque filler materials such as barium sulfate, bismuth trioxide, bismuth carbonate, powdered tantalum, or the like may be incorporated. Similarly, the diffuser element may comprise a reinforcement element(s) to provide for enhanced stiffness, to avoid kinking, etc. Such reinforcement element(s) can be, for example, a coil or braid that is on the outer surface of the diffuser element, within a wall of the diffuser element, or positioned on the inner wall of the diffuser element.

The dimensions of the diffuser element may vary according to many factors such as dimensions of the elongate body, desired diffusion rates, malady, subject's anatomy, and the like. The inner diameter, i.e., the diffusion space, of the diffuser element may be substantially the same throughout the entire length, or it may vary, e.g., it may be tapered, stepped or narrowed at any point along the length. For example the inner diameter may be tapered at the distal end or widened at any point along the length, e.g., widened over a distal portion or the inner diameter may be expanded to decrease drug concentration before delivery. For example, the inner diameter may contain a fluid, e.g., biological fluid from the external environment that dilutes the drug or agent.

Dilutor Element

In one embodiment, the device of the invention comprises a dilutor element to provide for dilution of the formulation as it passes through the device of the invention. The device can additionally comprise a diffuser element as described above. The dilutor element can be provided as an element separate from the diffuser element, or can be provided by an element that provides both functions (e.g., a combined diffuser/dilutor element). In general, the dilutor element comprises a selectively permeable material that allows for ingress of water from the environment of use, and thus provides for dilution of the formulation during its transit through the device.

The dilutor element generally comprise a material that is selectively water permeable, but substantially impermeable to formulation components, particularly to agent in the formulation, more particularly to ionized drug molecules or protons. The material of the dilutor element is generally chosen or adapted to be selectively permeable to water but impermeable to components of body fluids such as enzymes, peptides, proteins, etc. It should be noted that a polymer material can be chosen of such grade that the water sorption is between 10% to 80%, making the polymer permeable to water but still impermeable to formulation or its components, e.g., enzymes or proteins.

In use, water from the environment in which the device is implanted passes through the selectively water permeable modifying element, resulting in dilution of the formulation components during transit of the formulation through the device. At the same time, the volume of diluted formulation increases in proportion to the osmotic water influx and length of the selectively water permeable portion of the modifying element wall.

The dilution ratios and pumping rate at the exit at the device distal end is calculated as a function of selected device dimensions, e.g., the dimensions of the elongate body of the catheter and the associated dilutor element. In general, the dilution ratio of any chemical species at an undesirably high concentration ($C_o$) in a formulation to a more desirable concentration $C_L$, can be expressed as:

$$C_L/C_o = 1/(1+2\Phi_o/F_o)^{1/2} \quad (1)$$

where $\Phi_o$ is the water volume absorption rate through the selectively water permeable portion of the modifying element wall when filled with formulation (e.g., formulation having an agent at the same concentration as in the reservoir of a drug delivery device operably attached to the catheter), and $F_0$ is the rate of flow from the drug delivery device at the point of the catheter inlet.

For a cylindrical device (i.e., the elongate body and dilutor element define a cylindrical catheter body), $\Phi_o$ is defined as $$\Phi_o = (6.28 r K \Pi_o) L/h \quad (2)$$

where r is a mean radius of the elongate body, h is the thickness of the wall, K is water permeability, $\Pi_o$ is the osmotic pressure of the concentrated formulation in the drug delivery device, and L is the length of the selectively water permeable dilutor element.

Conservation of mass, when applied to the species being diluted, gives $$F_L C_L = F_o C_o \quad (3)$$

or $$F_L = F_o (C_o/C_L) = F_o (1+2\Phi o/Fo)^{1/2} \quad (4)$$

where $F_L$ is the flow rate of the formulation at the exit defined by the catheter distal end, and $C_L$ is the corresponding concentration at the exit. Detailed derivations of the equations above can be found in, for example, U.S. Pat. No. 4,298,003.

Suitable selectively water permeable materials suitable for use in the present invention include, but are not limited to polyether polyurethanes, plasticized cellulose acetates, silicone rubber, silicone elastomers, ethylene vinyl acetate copolymers, polyester elastomers (Hytrel®, Dupont), PEBAX®, cellulose esters(acetate, butyrate, styrene-butadiene block copolymer (Krator® Multibase, Inc.) and typically polymers with water sorption in the range of 10% to 80% such as hydrogel materials such as HERA.

Other Elements

The device of the invention can further comprise additional elements which are compatible for use in the device. For example, the device can comprise a modifying element that modifies the agent formulation during its transit through the device, such as those described in the U.S. patent application entitled "Catheter For Modification Of Agent Formulation,", filed on the same date as the instant specification and incorporated herein by reference in its entirety.

The modifying element facilitates modification of one or more physical or chemical properties of a formulation or component thereof (e.g., a drug or agent). The terms "modification" or "physical or chemical modification" as used herein generally means any physical or chemical change to a formulation and/or a component(s) of a formulation, including a physical or chemical change to an agent or drug in the formulation. Examples of "modifications" include, but are not necessarily limited to dilution or solubilization of a formulation component(s) (e.g., agent); increase or decrease in formulation pH; and production of an active species of an agent from an inactive species provided in the formulation (e.g., conversion of a prodrug to an active drug).

Thus, the physical or chemical modification facilitated by the modifying agent can be, for example, dilution or solubilization of the agent to be delivered; alteration in pH of the formulation; a change in the physical conformation of the agent being delivered; a chemical reaction that provides for conversion of an agent from a pharmaceutically inactive state to a pharmaceutically active state; and the like. The modifying agent can thus be a solvent (e.g., water or other fluid present in the environment surrounding the catheter (e.g., at the implantation site)); an enzyme; a buffer or other agent that adjusts pH; or a catalyst or other agent that can effect a desired physical or chemical modification. In embodiments where the modifying element facilitates dilution of the formulation, the modifying element acts as a dilutor element described herein.

In one embodiment, the modifying agent activates a previously inactive drug or therapeutic agent. By "activate" is generally meant an increase the biological activity, by, for example, altering the physical structure or conformation (e.g., to convert a prodrug to a drug), pH, etc., of the agent. For example, a drug that is unstable at or near neutral pH can be stably stored in the drug reservoir at a high or low pH and readjusted to neutrality during transit through the catheter. Similarly, an inactive protein may be stored in a stable state/conformation and then converted (e.g., cleaved, ionized, enzymatically converted, mixed with another species (i.e., agent drug), etc.), to an active state prior to delivery.

In one embodiment, modification is accomplished by incorporating a modifying agent as part of the catheter. In this embodiment, an agent is delivered through the catheter, contacts the modifying agent at some point in the flow path defined by the catheter, and is modified by the modifying agent of the modifying element prior to its release at the delivery site. The modifying element in this embodiment is that portion of the catheter comprising a modifying agent.

The modifying agent can be associated with at least an inner wall of the modifying element (i.e., a wall of the modifying element is in fluid communication with the catheter inner lumen defining the formulation flow path), and in some embodiments is incorporated into the body of the modifying element. As will be evident to the ordinarily skilled artisan, the modifying agent can be incorporated into the modifying element by impregnating, imbedding, coating, or chemically bonding the modifying agent on or within in the modifying element component as appropriate according to the component(s) with which the modifying agent is associated and the nature of the modifying agent. For example, the modifying agent can be coated on an inner wall, an outer wall, or both of the modifying element; impregnated in a modifying element wall; or any combination thereof. For example, the modifying agent can be a catalyst (e.g., an enzyme) immobilized on an inner surface of the modifying element, such that the immobilized catalyst serves to transform the agent into an active species prior to release of the agent from the catheter. Alternatively or in addition, the modifying agent may diffuse out of the catheter to reach with the diluent.

Where the modifying element is provided as a bulb- or ring-like element attached to the elongate body distal end, the modifying agent can also be provided as a solution, gel, semi-solid, or other material placed within a lumen or space defined by the modifying element (e.g., as a porous solid or semi-solid material within a lumen defined by the modifying element. The bulb- or ring-like element can be provided as an at least partially collapsible element to facilitate implantation.

The modifying element can be combined with other elements of the device of the invention. For example, a modifying agent can be combined with a diffuser element so that the diffuser element is adapted to provide for both modification of the formulation (e.g., the modifying element function) and diffusion of the formulation out of the device (e.g., diffuser element function).

Drug Delivery Devices

As discussed above, the device of the invention is generally associated with a drug delivery device. The drug delivery device supplies drug or therapeutic agent to the device for delivery to a delivery site.

The drug delivery device is generally comprises a drug reservoir that holds drug or agents to the delivered. Thus, the device enables long-term drug delivery without the need to re-fill or re-position the device. As such, the drug delivery device may be external to the subject or may be implanted. Regardless of whether the drug delivery device is external or implanted, the drug delivery device is associated with the device of the invention. By "associated" is meant attached, connected or the like to provide a pathway between the drug delivery device and the device. The association may be accomplished by a variety of means, e.g., chemical, mechanical or other such means. An attachment element, e.g., between the drug delivery device and the elongate body, may provide the means of association. As such, the drug delivery device may be associated with the elongate body, the diffuser element or both.

The entire drug delivery system, e.g., the drug delivery device, the elongate body and the diffuser element may be provided pre-assembled, separately or a combination thereof. In particular embodiments, the entire assembly or components thereof will be provided sterile. Sterility can be accomplished by a number of means commonly known to those of skill in the art, e.g., gamma sterilization, steam sterilization, ethylene oxide sterilization, plasma sterilization, and the like.

Drug delivery devices suitable for use in the invention may be based on any of a variety of modes of operation. For example, the drug release device can be any convective system (e.g., a system that causes mass movement of material out of the reservoir of the device by force (rather than by, for example, diffusion). For example, the drug release device can be an osmotic pump, an electroosmotic pump, a vapor pressure pump. In other embodiments, the drug release device is based upon an electrodiffusion system, an electrolytic pump, an effervescent pump, a piezoelectric pump, a hydrolytic system, an electrochemical pump, an electromechanical pump, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852, and the like. In general, the present methods of drug delivery can be accomplished using any of a variety of refillable, non-exchangeable pump systems. Pumps and other convective systems are generally preferred due to their generally more consistent, controlled release over time.

In one embodiment, the drug release device is a controlled drug release device in the form of an osmotically-driven device. Preferred osmotically-driven drug release systems are those that can provide for release of drug in a range of rates of from about 0.01 µl/day to about 100 µl/day (i.e., from about 0.0004 µl/hr to about 4 µl/hr), preferably from about 0.04 µl/day to about 10 µl/day, generally from about 0.2 µl/day to about 5 µl/day, typically from about 0.5 µl/day to about 10 µl/day. In one embodiment, the volume/time delivery rate is substantially constant and at a substantially consistent rate (e.g., delivery is generally at a rate± about 5% to 10% of the cited volume over the cited time period, e.g., a volume rate of about 500 µl/day is accomplished by delivery of about 20 µl/hour over a period of 24 hours, with the delivery rate over that 24 hours period fluctuating over that period by about ±5% to 10%). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In one embodiment the controlled drug release device is an osmotic pump, e.g., an osmotic pump similar to that described in U.S. Pat. No. 5,728,396. In one embodiment of particular interest, the osmotic pump is a DUROS™ osmotic pump. In another embodiment of particular interest, the controlled drug release device is an electrolytic pump, such as provided by Microlin, and by Med-E-Cell™ as Infu-Disk™.

Methods of Use

The device assembly of the present invention is described herein primarily as used in drug delivery for simplicity and ease of disclosure. Any of a wide variety of drugs or therapeutic agents can be delivered using the present invention. Drugs suitable for use are generally in flowable formulations and are typically provided as liquids or semi-solids. The drugs may be anhydrous or aqueous solutions, suspensions or complexes and may be formulated with pharmaceutically acceptable vehicles or carriers, as well as inert or active ingredients. The drugs of formulations suitable for delivery using the present invention may be in various forms, such as uncharged molecules, components of molecular complexes or pharmacologically acceptable salts. Also, simple derivatives of the agents, e.g., prodrugs, esters, ethers, amides and the like, that are easily hydrolyzed by body pH, enzymes and the like can be employed. Preferably, the drugs are formulated so as to remain stable for long periods of time. As such, drugs or formulations of drugs may be stored in a drug reservoir in an inactive state and subsequently converted to an active state prior to delivery. Such conversion, i.e., activation, may be accomplished in or on a variety of locations in the system. As stated above, means for activation may take place in the elongate body or the diffuser element. Similarly, the conversion may be effected in the drug delivery device, e.g., in the drug delivery device distal orifice, or the like or may take place in a combination of the aforementioned.

Other uses of the described invention will be apparent to others skilled in the art upon reading the present disclosure, however, and the present invention is intended to encompass such uses.

The diseases and conditions for which the present invention may find use vary. Of particular interest is the treatment of diseases or conditions that require long-term therapy, e.g., chronic or persistent diseases or conditions for which therapy involves treatment over a period of several days, weeks, months or years, up to the remaining lifetime of the subject. The present invention is particularly suited for long-term therapy, and in particular for therapy to treatment sites of the body inaccessible to conventional drug delivery devices or to fragile regions of treatment.

In the subject methods, the device assembly is navigated to a delivery site within a subject, e.g. through biologically defined lumens or preformed guides, etc. Insertion of the device assembly into the subject is generally accomplished in a manner similar to insertion of any of a variety of devices known to those of ordinary skill in the art, e.g., under aseptic conditions, with at least some local or general anesthesia, under fluoroscopy, etc. The device of the invention is preferably associated with a drug delivery device which comprises a drug reservoir, and the assembly may be pre-loaded with drug or therapeutic agent. Pre-loading reduces start-up times, i.e., time related to movement of the drug or agent from the drug delivery device to the delivery site. This feature is particularly advantageous where the drug delivery device releases drug at a low or very low volume rate, e.g., in the range of about 0.1 µl per day to 200 µl per day. The pre-filled drug or agent may be the same or may be a different drug or agent as that which is to be delivered over the course of the treatment, or may be a different formulation thereof. The drug delivery device may be associated with the device of the invention at the beginning of the procedure. However, it is, of course, also possible to associate the drug delivery device with the device after the device has been positioned in the subject.

In practicing the subject methods, the device may be implanted in the subject for a chronic period (e.g., over several days, weeks, months or years). However, the device may also be designed for temporary use. The associated drug delivery device may be implanted in the subject or may be external to the subject and may be fixedly or removably attached to the device. Where the drug delivery device is removably attached, it may be removed following a desired treatment regime and where desirable, replaced with a similar or different drug or agent.

In certain embodiments, the drug delivery device and/or device may be anchored within the subject by any suitable means. For example, sutures can be used to secure the drug delivery device and/or device at or near an implantation site. Following implantation, the device of the invention defines a drug delivery conduit that provides for transport of drug or other therapeutic agent from the proximal end to the distal end of the device, where the proximal end is preferably maintained at the initial access or implantation site and the distal end is positioned at or near the treatment site.

Similarly, treatment sites and subjects may vary. For example, the device with associated drug delivery device may be used and/or implanted at any convenient site within a subject's body and oriented for delivery to any desired delivery site. For example, the device assembly and/or drug delivery device may be partially or completely implanted in the subject, with at least a portion of the drug delivery device retained at an accessible, external or subcutaneous site within or outside the subject's body, e.g., under the skin of the arm, shoulder, groin, neck, back, leg or the like or within a surgically created or natural body cavity, e.g., within the mouth or surgically created pocket. Typically, the present invention will find use in subjects presently suffering from a disease or condition. However, subjects not presently suffering from a disease or condition, but who are susceptible to such, may also benefit from the present invention, for example for the delivery of prophylactic therapy regimes.

The device assembly may be positioned at a site close e.g., within a few inches or fraction(s) thereof, or at a site relatively distant, (e.g., more than about 5 inches, generally more than about 10 inches to 20 inches, typically more than about 40 inches) to a selected delivery site. A single device assembly or a plurality of device assemblies can be used and/or implanted in a subject during the course of a treatment program depending on the extent of the treatment, the desirability of administering to multiple sites, and the like.

The device of the invention can be used to deliver any of a wide variety of substances. In one exemplary embodiment the device comprises an elongate catheter body and with diffuser element is used to deliver insulin, where the insulin is contained in a drug delivery device, which is in turn operatively connected to a device assembly of the invention. A distal end of the device assembly is implanted subcutaneously to provide for delivery of insulin to the subject.

EXEMPLARY EMBODIMENTS

Exemplary embodiments of the invention are provided in the figures. Referring to FIGS. 1-3, the device 10 comprises elongate body 20 operatively associated with diffuser element 30. Elongate body 20 comprises proximal end 21 defining inlet 22, distal end 23 defining outlet 24, and wall 25 defining a lumen or passageway 26, which passageway extends between the proximal and distal ends 21, 23. As illustrated in FIGS. 1 and 3, elongate body 20 and diffuser element 30 can be operatively associated by attachment to each other (e.g., by attachment element 40). Alternatively, as illustrated in FIG. 2, elongate body 20 and diffuser element 30 can be operatively associated by attachment to a drug delivery device 80 (e.g., elongate body 20 and diffuser element 30 are each separately attached to the drug delivery device 80) to provide drug delivery system 100. In either configuration, elongate body 20 and diffuser element 30 are associated so as to define a diffusion space 35 between an outer wall of elongate body 20 and an inner wall of diffuser element 30. Attachment of the elongate body and diffuser element to each other can be accomplished by, for example, use of an attachment element (e.g., an adhesive, clamp, etc, and/or by ultrasonic welding, molding, and the like), and/or by any of a variety of attachment elements known in the art (e.g., press fit locks, luer locks, mechanical clamping, chemically bonding, adhesive bonding, ultra sonic welding, heat welding, and the like). The attachment site between elongate body 20 and diffuser element 30 can be covered by a sheath or other element to provide for a smooth surface to facilitate implantation.

In FIG. 4, diffuser element 30 is in the form of a ring or donut-shaped element, and is operatively attached to the distal end of elongate body 20, e.g., to circle a desired anatomical structure. In this configuration, diffusion space 35 is provided within a lumen defined by the diffuser element. In FIG. 5, diffuser element 30 is provided as a bulb-like projection attached to elongate body distal end 23.

In another exemplary embodiment of interest, the device comprises diffuser element 30 and dilutor element 60. As exemplified in FIG. 6, dilutor element 60 can be positioned along a portion of elongate body 20. Dilutor element 60 may be provided as a patch-like element within or attached to elongate body wall 25, or, as exemplified in FIG. 6, dilutor element 60 may be provided as an element that substantially surrounds the flow pathway through elongate body lumen 26. Where used in combination with a separate diffuser element, diffuser element 30 can be positioned at a site distal (e.g., "downstream" in the flow pathway toward the device outlet) relative to dilutor element 60 (as illustrated in FIG. 6), or can be positioned within a wall of diffuser element 30. Dilutor element 60 is selectively permeable to water in the environment of use. Water enters elongate body lumen 26 by diffusion through dilutor element 60 (noted by arrows 65) to dilute formulation as it flows through lumen 26, Attachment of the device components (e.g., elongate body 20, dilutor element 60, and diffuser element 30) can be accomplished by, for example, use of an attachment element (e.g., an adhesive, clamp, etc, and/or by ultrasonic welding, molding, and the like), and/or by any of a variety of attachment elements known in the art (e.g., press fit locks, luer locks, mechanical clamping, chemically bonding, adhesive bonding, ultra sonic welding, heat welding, and the like). Again, attachment sites can be covered by a sheath or other element to provide for a smooth surface to facilitate implantation.

Figure 7:
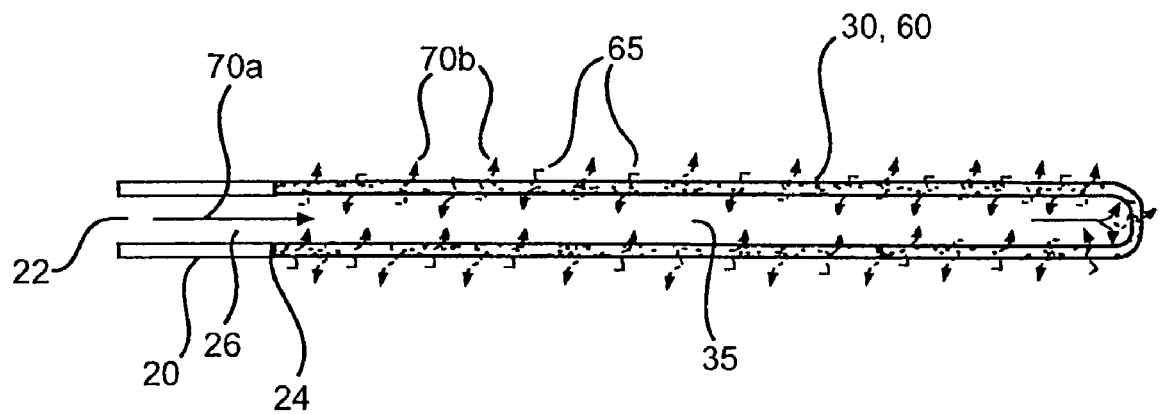
FIG. 7 is cut-away view of a local concentration management system of the invention comprising an elongate body having both dilutor element and diffuser element properties.

In one embodiment of particular interest the diffuser element and the dilutor element are provided as a single diffuser/dilutor element. In one embodiment, exemplified in FIG. 7, the diffuser/dilutor element 30,60 is configured as a thin walled membrane structure, e.g., wall thickness in the range of about 2 to 20 thousands of an inch. This thin wall structure is supported by elongate member 20 with a clearance gap of less than 5 thousands of an inch. Structural strength is provided by elongate member 20 for which the device provides dilution and dispersion of the drug concentrations from the delivery system. Elongate member 20 can also be selected to be semipermeable to allow water from body fluids to be absorbed and dilute the drug concentration. The diffuser/dilutor element can be attached (e.g., chemically bonded or bound with adhesive or the like, and/or through use of an attachment element as described above) to a substantially formulation impermeable elongate body at any site along the length of elongate body 20 (e.g., at a distal end portion, at a site along a elongate body 20 wall, at a proximal end portion (e.g., to provide a sheath for substantially the length of elongate body 20, etc.).

Figure 8A:
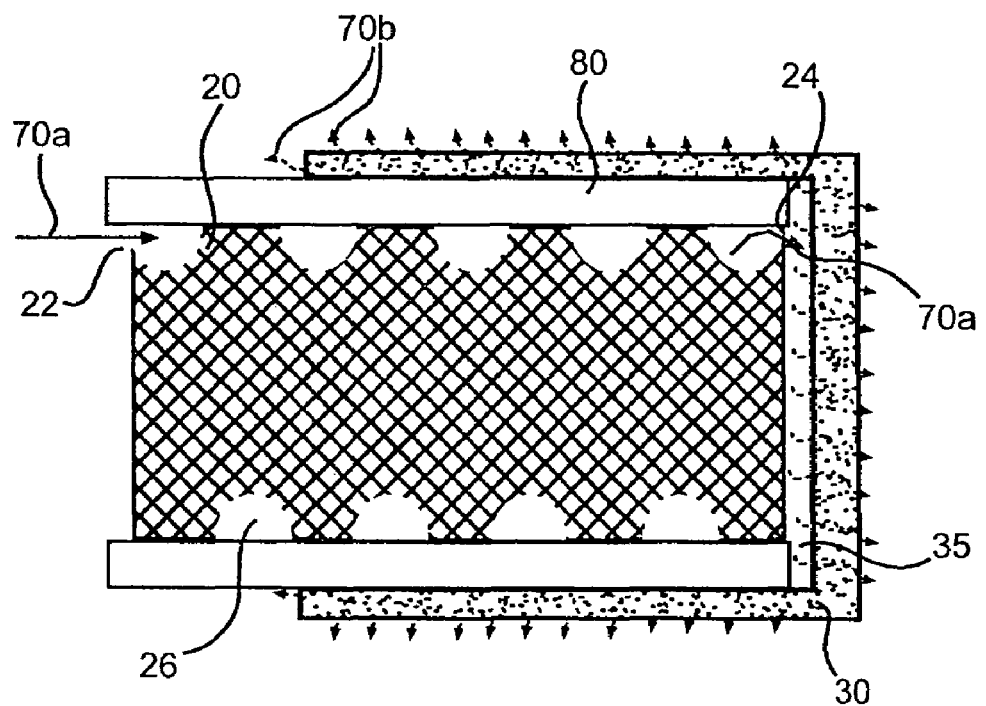
FIGS. 8A and 8B are a cut-away views of local concentration management systems of the invention in which elongate body 20 defined by an exit orifice 80 of a drug delivery device.
Figure 8B:
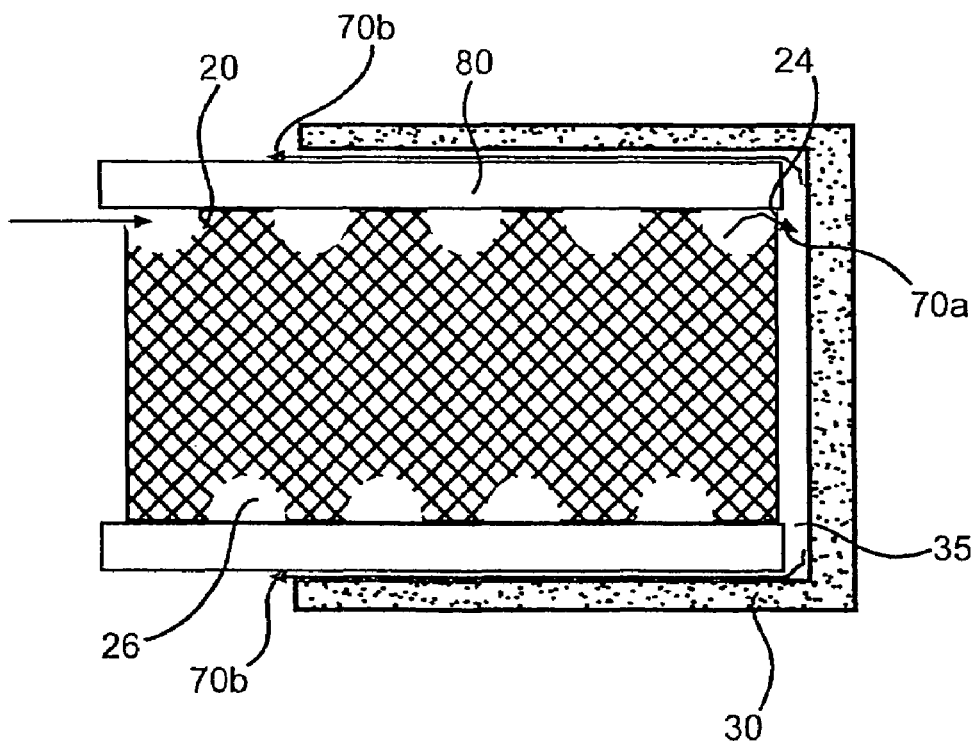

In another embodiment, exemplified in FIGS. 8A and 8B, elongate body 20 is defined by an exit orifice of a drug delivery device 80. In this embodiment, diffuser element 30 is provided in a hat or cup configuration at a distal end of drug delivery device 80, and in fluid communication with lumen 26 of elongate body 20. Diffuser element 30 is operably associated with elongate body 20 by securing diffuser element 30 to an outside portion of drug delivery device 80. An inner wall of diffuser element 30 defines diffusion space 35 into which formulation flows. Diffuser element 30 may comprise a dilutor element (not shown) within a diffuser element wall. Alternatively, a diffuser/dilutor element, which combines both the diffuser and dilutor element functions to provide for diffusion of formulation through a wall of the element 30, can be provided in the configuration exemplified in FIG. 8A.

As illustrated in each of Figures, formulation introduced into elongate body inlet 22 flows (as generally indicated by arrow 70a) through and out the device (indicated by arrows 70b). Where device 10 comprises diffuser element 30 (as illustrated in FIGS. 1-8), formulation flows through elongate body passageway 26, out outlet 24, and into diffusion space 35. Formulation can spread within diffusion space 35. Where the device comprises a dilutor element (or combination dilutor/diffuser element), the formulation is diluted by water that enters the device via selectively water permeable dilutor element 60 prior to or after the formulation flows into diffusion space 35. Where device 10 comprises a dilutor element, the formulation contacts dilutor element 60 either along a portion of flow pathway 70a (see, e.g., FIG. 6) along flow pathway 70a'(see, e.g., FIG. 6) or both. Formulation diffuses out diffuser element 30 as illustrated by arrows 70b. Diffuser element 30 thus increases the surface area over which formulation is delivered, effectively diluting the formulation in the environmental fluids surrounding the catheter.

EXAMPLES

The following examples are presented to illustrate the present invention and to assist one of ordinary skill in making and using the same. The examples are not intended in any way to otherwise limit the scope of the invention.

Example 1

Polymeric Cup as Diffuser Element

Polymeric film is shaped into a diffuser element having a "cup" or "hat" configuration, and is placed over an exit outlet of a drug delivery device, such that the elongate body of the device is actually contained within the body of the drug delivery device (FIG. 8). The diffuser element serves as a secondary rate control means, and capture bursts of formulation that may be released from the drug delivery device.

The following is an estimate of normalized permeability of suitable polymeric materials for such polymeric diffuser elements for use in delivery of a sufentanil formulation from a drug delivery device, e.g., an osmotic pump. The following assumptions were made in calculating the permeablities of the polymeric materials:

Minimum release rate of agent from device: 2.5 µg/hr
Maximum release rate of agent from device: 20 µg/hr
Diffuser element configuration and dimensions: a cylinder having a diameter of 0.3 cm and length of 0.6 cm, with a thickness of 0.0038 cm (or 1.5 mils).
Total formulation diffusion area: 0.64 cm$^2$
Melting point of sufentanil: 97° C. or 370K
The $DC_s$ values are calculated as follows:
Minimum value=$(2.5/3600)(0.0037/0.64)=4.1 \times 10^{-6}$ µg/cm sec
Maximum value=$(20/3600)(0.0038/0.64)=3.3 \times 10^{-5}$ µg/cm sec)

Suitable polymeric material(s) that correspond to these $DC_s$ values may be found in the published data of Michaels et al. (AICHE J. 21(6) (1975)). The calculated $DC_s$ values as a function of melting point (MP) are provided in FIG. 9. The equations for each of the materials, and the correlation coefficients (R) are provided in FIG. 9.

Figure 9:
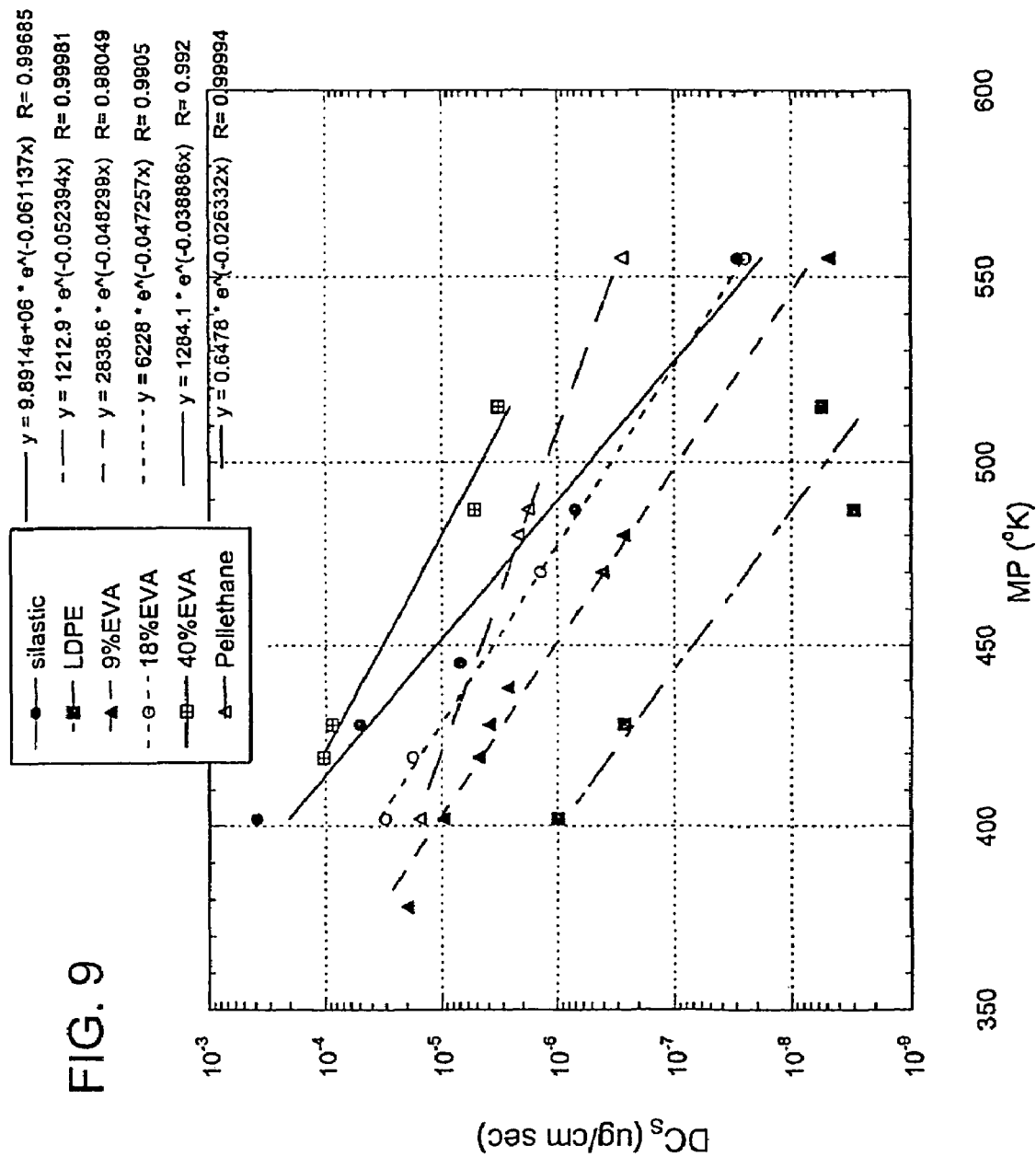
FIG. 9 is a graph showing the association of $DC_s$ with melting point (MP) of a polymeric material, where D is the diffusivity of an agent in the polymer and $C_s$ is the concentration of the substance or agent in the polymer. Closed circle, silastic; closed square, low density polyethylene (LDPE); closed triangle, 9% ethylene vinyl acetate (EVA); open circle, 18% EVA; hatched square, 40% EVA; open triangle pellethane.

As illustrated in FIG. 9, some low density polyethylenes or ethylene vinyl acetate (EVA) copolymers with vinyl acetate (VA) contents lower than 9% are within an appropriate $DC_s$ range. $DC_s$ values will change as the dimensions of the diffuser vary. Because $DC_s$ is sensitive to the diffusional area and thickness of the membrane, these two parameters can be varied in order to obtain the desired DCs value. It should be noted that thickness of the membrane will impact the initial time lag of delivery, thus may be less desirable to increase over a suitable thickness where this is a concern.

Example 2

Delivery of Baclofen HCl

A Baclofen HCl solution in DMSO (335.8 mg/cc) was delivered using a prototype of a catheter of the invention. With reference to the equations described herein, the dilution ratio was calculated, with Co=335.8 mg/cc Baclofen, with $KΠo=31.3$ µl mils/cm$^2$ hr for the Silastic tubing (Dow Corning Q 4750). The outer diameter of the tubing (OD) was 0.047 in (0.0597 cm), while the inner diameter was inner diameter (ID) was 0.025 in (0.0317 cm). The mean diameter (calculated by taking the log average value due to variations in wall thickness) was 0.0443 cm, with a tubing wall thickness of 11 mils (0.0235 in minus 0.0125 in). The pumping rate was 20 µl/day (0.083 µl/hr). The length of the elongate body catheter was 5.22 cm.

Using these values and Equation (2) above, Φo is calculated to be 4.13 µl/hr. Using this value in Equation (3), the estimated flow rate at the exit of the Silasitc tubing (elongate body) should be $F_f=0.083 (1+2 \times 4.13/0.083)^{1/2}=0.83$ µl/hr.

Thus, according to this calculation, the flow rate at the delivery outlet of the Silastic tubing is about 10 times greater than the flow rate at the inlet connected to the pump. From Equation (1), the dilution ration can be calculated as Ct/Co=0.1.

An osmotic pump (DUROS™) was connected to an elongate body comprising a catheter coupled with a length of Silastic™ tubing having the same ID and OD as described above. The pump was filled with baclofen HCl in 100% DMSO (drug concentration (Co) 336.5 mg/cc), with the pumping rate determined to be about 3.48 µl/day (0.145 µl/hr). A mark was placed on the catheter at 5.22 cm from the connector to the pump. The pump and the section of catheter up to the mark were immersed in a water bath at 37° C. for ten days, after which the pumps were removed. The catheter were clamped at slightly above the 5.22 cm marks, and cut with a pair of scissors. The drug solution above the 5.22 cm mark was collected in separate flaks. Each catheter was further rinsed three times with 150 µl deionized water using a Hamilton syringe. The drug solution and the rinse were combined with diluted to volume for HPLC analysis to determine drug concentration. The experimental values are provided in the table below.

| Pump test | Distance drug solution traveled above the 5.22 cm mark (cm) | Total volume of drug solution above 5.22 cm mark (cc) | Drug concentration (Ct) in Silastic catheter above the 5.22 cm mark (mg/cc) | Dilution Ratio Ct/Co (Co = 336.5 mg/cc) |
|---|---|---|---|---|
| Pump 1 | 5.3 | 0.0168 | 54.8 | 0.163 |
| Pump 2 | 7.5 | 0.0238 | 72.3 | 0.215 |

The calculated drug dilution ratio from equation (1) and the values of Φo and Fo, Ct/Co=1/(1+2×4.13/0.145)1/=0.131. The experimental values for the dilution ratio Ct/Co were 0.163 and 0.215 from duplicate tests, which values are in the same order of magnitude and in good agreement with the calculated value. The main source of discrepancies between the predicted and actual values may be generally due to inaccuracies involved in estimating the Φo or KΠo values for the baclofen HCl solution. The KΠo values, and hence the Φo value, may have been overestimated.

The invention as shown and described is considered to be the one of the most practical and preferred embodiments. It is recognized, however, that the departures may be made therefrom which are within the scope of the invention and that obvious modifications will occur to one skilled in the art upon reading this disclosure.

What is claimed is:

1. A method for delivery of an agent to a delivery site in a subject, the method comprising the steps of:
    (a) implanting at the delivery site at least a distal portion of a device, the device comprising:
        an elongate body comprising a proximal end defining an inlet, and a distal end defining an outlet, the elongate body defining a lumen in the elongate body, said lumen extending between the proximal and distal ends; and
        a diffuser element operatively associated with the elongate body so as to define a diffusion space, wherein the elongate body distal end outlet is disposed in and in fluid communication with the diffusion space, wherein the diffuser element is drug-permeable and water-permeable so as to provide for dilution of a drug in the diffusion space and movement of drug out of the device; and (b) introducing into the elongate body inlet a drug at a first concentration, wherein said drug moves through the elongate body lumen, out the elongate body outlet, and into the diffusion space, and further wherein water from the environment outside the device passes into the diffusion space through the diffuser element to dilute drug in the diffusion space to a second concentration, and wherein said diluted drug diffuses out through the diffuser element to exit the device at the delivery site in the subject.

2. The method of claim 1, wherein the diffuser element comprises a semipermeable membrane, a microporous membrane or an ion exchange membrane.

3. The method of claim 1, wherein the distal outlet of the elongate body is defined by an exit orifice of a drug delivery device and the diffuser element is a cap in which the exit orifice is disposed.

4. The method of claim 1, wherein the diffusion space is defined by an outer wall of the elongate body and an inner wall of the diffuser element.

5. The method of claim 1, wherein said diffuser element surrounds at least a portion of said elongate body.

6. The method of claim 1, wherein the diffuser element is microporous.

7. The method of claim 1, wherein the diffuser element is a dense membrane.

8. The method of claim 1, wherein the diffuser element is an ion-exchange membrane.

9. The method of claim 1, wherein a diffuser element distal end extends distally beyond the elongate body distal end.

10. The method of claim 1, wherein the diffuser element is a ring-shaped element.

11. The method of claim 1, wherein the diffuser element is selectively permeable to water.

12. The method of claim 1, wherein the elongate body lumen is adapted for delivery of agent at a low volume rate.

13. The method of claim 1, wherein the formulation is introduced into the inlet at a low volume rate.

14. The method of claim 1, wherein the diffuser element comprises a polymeric film.

15. The method of claim 14 wherein the diffuser element has a Diffusion Coefficient (DC) value in the range between $4.1 \times 10^{-6}$ and $3.3 \times 10^{-5}$ µg/cm/sec.

16. The method of claim 1, wherein the elongate body is drug-impermeable, and further wherein the diffuser element is substantially impermeable to drug and selectively permeable to water.

17. The method of claim 1, wherein the elongate body lumen is at least partially filled with a drug formulation prior to said implanting.

18. The method of claim 1, wherein the diffuser element is substantially impermeable to biological fluids or components of biological fluids.

* * * * *